(12) United States Patent
Cinquin et al.

(10) Patent No.: US 6,932,089 B1
(45) Date of Patent: Aug. 23, 2005

(54) REMOTELY CONTROLLABLE SYSTEM FOR POSITIONING ON A PATIENT AN OBSERVATION/INTERVENTION DEVICE

(75) Inventors: Philippe Cinquin, La Tronche (FR); Jocelyne Troccaz, Eybens (FR)

(73) Assignee: Universite Joseph Fourier, Grenoble (FR)

( * ) Notice: Subject to any disclaimer, the term of this patent is extended or adjusted under 35 U.S.C. 154(b) by 0 days.

(21) Appl. No.: 10/031,053

(22) PCT Filed: Jul. 15, 1999

(86) PCT No.: PCT/FR00/02042

§ 371 (c)(1),
(2), (4) Date: Nov. 8, 2002

(87) PCT Pub. No.: WO01/05319

PCT Pub. Date: Jan. 25, 2001

(30) Foreign Application Priority Data

Jul. 15, 1999 (FR) .................................. 99 09363

(51) Int. Cl.⁷ ............................................. A61B 19/00
(52) U.S. Cl. ...................... 128/897; 378/195; 378/197; 269/55

(58) Field of Search .................. 128/897–98; 600/437, 600/459; 73/618; 378/167, 189, 193–198; 269/55–58

(56) References Cited

U.S. PATENT DOCUMENTS

| | | | |
|---|---|---|---|
| 4,291,578 A | 9/1981 | Hetz et al. | ..................... 73/633 |
| 4,489,729 A | 12/1984 | Sorenson et al. | ........... 128/660 |
| 5,010,564 A | 4/1991 | Thomas | ...................... 378/176 |
| 5,048,529 A | 9/1991 | Blumenthal | .............. 128/660.1 |
| 5,175,754 A | 12/1992 | Casey et al. | ..................... 378/4 |
| 5,428,660 A | 6/1995 | Daniel, Jr. | .................. 378/197 |
| 5,474,072 A | 12/1995 | Shmulewitz | ........... 128/600.09 |

FOREIGN PATENT DOCUMENTS

GB 1348154 3/1974

*Primary Examiner*—John P. Lacyk
(74) *Attorney, Agent, or Firm*—Duane Morris LLP

(57) ABSTRACT

A remotely controllable system for positioning on a patient an observation and/or intervention device, including a frame to which the device is bound with a number of degrees of freedom; flexible connection means, each of which is arranged between the frame and a point attached to the patient's support or to the patient himself; remotely controlled means for modifying the length/tension of the binding means; and means for remotely observing the device behavior.

14 Claims, 2 Drawing Sheets

REMOTELY CONTROLLABLE SYSTEM FOR POSITIONING ON A PATIENT AN OBSERVATION/INTERVENTION DEVICE

BACKGROUND OF THE INVENTION

The present invention relates to a remotely controllable system for positioning a mobile observation and/or intervention system on a patient. It applies, for example, to medical analysis systems, such as endoscopic or echographic systems or to simple invasive devices such as a puncture needle. It will more specifically be described in the context of the use of an echographic probe (remote echography).

Echography is a very advantageous imaging modality, because of its lightness, harmlessness, and its richness in morphological and functional information. Its implementation requires a particular specialization. Several clinical situations would require for the examination to be performed by telemedicine means.

The simplest solution, used in some telemedicine operations, is for a local operator to put himself in vocal and possibly video connection with a distant expert doctor. It could then be devised for the nurse or even for the patient himself to handle an echographic probe and for the distant expert to guide him and draw a diagnosis therefrom. Such resorting to a distant expert is used in several medical situations but applies with difficulty to echography. Indeed, in echography, the performing and interpretation of the examination are intimately connected. Only the operator, who has controlled the way in which the echographic probe has been displaced on the patient's body, has all the information useful for the interpretation. This feature makes remote echography operations difficult. The local operator must already be relatively well trained, and the remote expert must be able to precisely indicate to him the probe displacements to be performed. Now, such displacements imply 6 degrees of freedom (three translations and three rotations). It can be understood that the expression by the remote expert of the displacement orders in vocal form, and even more their execution by the local operator, may be difficult.

To overcome the disadvantages of the above-mentioned simple remote echography, it would be necessary to enable the distant expert to take control of the displacement of the echographic probe, for example, by controlling a probe assembled on a remote-controlled robot. Such systems using robotics are used in medicine and especially in surgery. For this purpose, robotic architectures of master-slave type are typically used, in which a remote operator has a stress feedback system which enables him to displace a virtual object according to n degrees of freedom and in which a slave system placed close to the patient reproduces the master's motions while said master can feel a resistance to its motion.

In the conventional approach, the master and the slave execute exactly the same motions, the slave being linked to a referential with respect to which the patient's position must be located. The mechanical constraints to which the slave is submitted must remain within limits compatible with the possibilities of synthesis of a stress feedback by the master. Besides, the used mechanical architectures use rigid and relatively heavy structures, even when the useful load has a weight smaller than 10 N. It is thus imperative to design high-performance security systems, able to forbid uncontrolled motions of the robot, which would be likely to harm the patient or the medical and surgical team surrounding him.

FIG. 1 shows a very simplified side view of a patient 1 lying on a table 3 for a conventionally remotely controlled echographic examination. An echographic probe 5 is arranged to contact the patient, for example, his abdomen, by an articulated and remote controlled robot arm system 7. Such a system implies a heavy computer architecture to ensure the control and stress feedback. It should be noted that the slave (supporting the echographic probe) contacts the human body, which exerts against it variable and widely unpredictable pressures. This requires, if the system is desired to securely operate, implementing an extremely complex system. Due to all these constraints, the slave is a costly system.

The dilemma thus currently is the following: to use a local operator guided by a distant expert, which appears to be poorly adapted, or to use a robotic system, having a particularly heavy and expensive mechanical structure and associated computer system.

More generally, the above problem, that is, to provide a low-cost secure remotely controlled positioning system, is posed in many other cases falling or not within the medical field. In the medical field, a problem of the same type is posed, for example, for the remote control in orientation and in position of an endoscope or a puncture needle.

Operations performed under endoscopy grow in number. They require introduction of various tools of generally cylindrical shape through the skin. The number of these tools may be such that the operator is disturbed by its assistants which maintain them for him in an adequate position. For this and other reasons, various systems have been developed to bear and position tools penetrating into the human body upon interventions under endoscopy. These systems are "conventional" robots, which are fastened to the operating table or to the ground, and which displace the tools that they support to the coordinates which are communicated thereto by various interfaces with the user, or even, in some cases, by control of the images observed by the endoscope. Such systems remain heavy and require specific adaptation to take into account security problems linked to the use of relatively rigid systems supporting surgical instruments.

The puncture of various organs of the human body is a widely used method to sharpen a diagnosis (sampling of material for microscopic analyses, measurement of various physical, and especially electric characteristics . . . ), or for therapy (physical, mechanical, chemical, electric destruction . . . ). In many cases, the puncture is performed under control of imaging means (radio, echography, scanner, MRI . . . ). It may be advantageous to robotize the positioning of the puncture needle, which opens up the way to the automated implementation of the puncture gesture in several clinical situations, among which, in particular:

a physically limited access to the patient (scanner, MRI . . . ), the need to perform the gesture rapidly, and the need to perform the gesture from a distance.

Again, existing remotely controlled robotization and positioning systems are too heavy to enable easy generalization of this type of application.

BRIEF SUMMARY OF THE INVENTION

Thus, an object of the present invention is to provide a remotely controlled system for positioning a diagnosis or therapeutic device which is relatively simple.

Another object of the present invention is to provide such a system which has a low cost while avoiding any risk for the patient and the people around him.

Another object of the present invention is to provide such a system in which it can be passed from a remote control to a local handling of the controlled device.

Another object of the present invention is to provide a specific remotely controllable device for displacing an object.

To achieve these objects, the present invention generally provides a remotely controllable system for positioning a useful load, in which:

the components exhibit compliance features, that is, are likely to reversibly deform under the effect of moderate mechanical constraints, external to the system (this implies in particular that the system be not only formed of rigid arms); and the motions tend to reproduce the order of a remote operator, but taking account of the system environment, especially of the topography of the site in which is placed the device having a remotely controlled displacement (light control), and without it being necessary to know at any time the geometric characteristics of the various system components.

Such a system thus differs from conventional robots, most of the components of which are rigid, and in which a compliance can only be obtained by specific characteristics of the joints between the rigid elements, and the control of which implies as fine a knowledge as possible of the geometric characteristics of the robot, a coordinate changer typically enabling passing from the "articular" coordinates of the robot to the Cartesian coordinates, by means of a model of the robot.

The "compliance" and "light control" properties are particularly well adapted to medicine applications, when diagnosis or therapeutic tools are desired to be displaced on the human body. The compliance enables having the system and the tools that it bears directly contact the patient (whose body may even be used to help supporting the system and its useful load). The light control cannot be a handicap; indeed, the precise knowledge of the position of the system and of the controlled device in a referential external to the patient (provided by the "conventional" control) teaches much less than the knowledge of the position of the useful load with respect to the anatomic or therapeutic targets of the human body. Now, this relative position information can be provided by the controlled device itself, by various sensors, or by learning.

More specifically, the present invention provides a remotely controllable system for positioning on a patient an observation and/or intervention device including a frame to which the device is bound with a number of degrees of freedom; flexible connection means, each of which is arranged between the frame and a point attached to the patient's support or to the patient himself; remotely controlled means for modifying the length/tension of the binding means; and means for remotely observing the device behavior.

According to an embodiment of the present invention, each of the flexible binding means is of cable, thread, or strap type.

According to an embodiment of the present invention, each of the flexible binding means is resilient.

According to an embodiment of the present invention, the remotely controlled means include winder motors.

According to an embodiment of the present invention, the remotely controlled means include artificial muscles.

According to an embodiment of the present invention, the connection between the frame and the device is ensured by remotely controlled flexible binding means.

According to an embodiment of the present invention, the device is an echographic probe, and said remote observation means enable observation of the echographic image.

According to an embodiment of the present invention, the device is an endoscope, and the remote observation means enable observation of the endoscopic image.

According to an embodiment of the present invention, the device is a needle holder, and the remote observation means enable observation of an image of scanner, MRI, . . . type.

According to an embodiment of the present invention, the link between the patient and the distant remote-control central station includes an audio link.

The foregoing objects, features and advantages of the present invention, will be discussed in detail in the following non-limiting description of specific embodiments in connection with the accompanying drawings.

DETAILED DESCRIPTION OF THE INVENTION

The present invention will first be more specifically described in the context of the use of an echographic probe (remote echography).

The present invention is based on an analysis of the actual needs of a remote echography operation. The distant expert must be able to:

have a general vision of the scene, and dialog with the patient and with the local staff, control the acquisition parameters of the echograph, visualize the echographic images, indicate, by displacing a virtual probe, the direction of the desired displacements of the real probe (six degrees of freedom), displace the real probe according to these indications, control on the echographic images the way in which the displacement orders are really taken into account, adapt the orders to the way in which they are executed and to needs, possibly have, from the virtual probe, an information feedback concerning the pressure exerted by the real probe on the patient.

The patient or a local operator must also be able to:

initialize the probe displacement system, interrupt the probe displacement if it becomes painful (too high a pressure, for example), give back the control to the expert after such an interruption; and possibly manually displace the probe, according to the expert's vocal indications, to face specific situations.

The applicant has found that these requirements could be better fulfilled with a remotely controlled system having a compliant structure and a light control than with a master-slave type robot of rigid structure such as previously described. Further, the use of a flexible or compliant remote displacement structure avoids forbidding any motion to the patient during an analysis, which, in the case of an echography, may be relatively long.

According to an aspect of the present invention, the applicant has noted that, in fact, when an echography is performed, the expert has a sufficient indication of the motions that the probe has performed and that it desires it to perform from the echograhic image that he receives. For him to know exactly the probe positioning with respect to the patient matters little. It is enough that, from a given positioning, he can perform a displacement roughly in a desired direction (translation, rotation) and that, after each incremental displacement, he can decide whether he desires to continue the displacement in the same direction or move in another direction to better see what is desired to be observed. Thus, the present invention provides suppression of any rigid connection between the probe and the patient's support. Further, the echographic probe sustentation or suspension function is suppressed. The system displaces the probe on the patient's body while said probe rests on said body.

Figure 1:
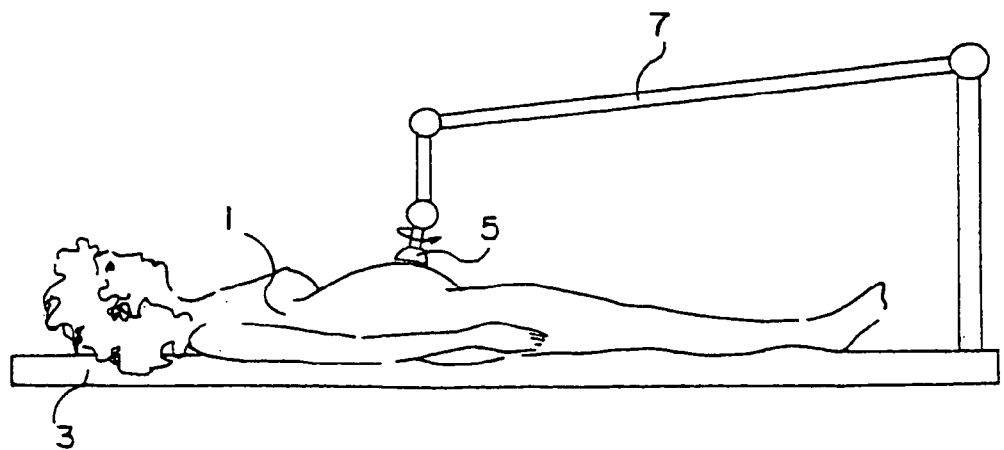
FIG. 1 shows a remote echography system using conventional robotic techniques.
Figure 2:
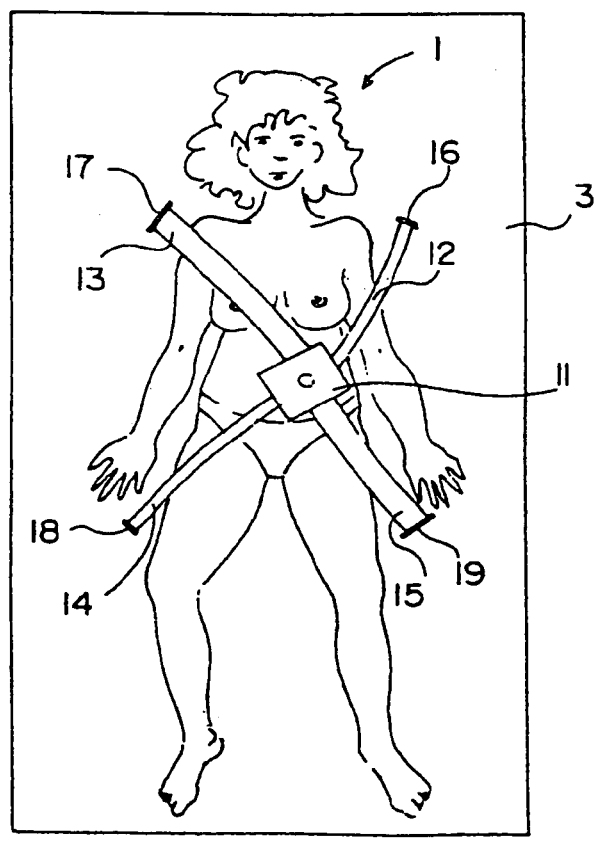
FIG. 2 is a very simplified top view of a remote echography system according to the present invention.

FIG. 2 shows an embodiment of the present invention. A patient 1 lying on a table 3 is considered again. Echographic probe 5 moves along with a frame 11 laid on the patient's body. According to the present invention, various flexible mechanical means such as straps, threads, cables, or the like are provided to have frame 11 of a probe slide on the patient's body around a selected location. For example, in the embodiment shown, frame 11 is attached to four straps 12, 13, 14, and 15, the second ends of which are attached at points 16, 17, 18, and 19. Points 16 to 19 may for example be binding points attached to table 3. They also may be binding points attached to straps respectively arranged around the patient's arms and thighs. It should be understood that by providing at the level of the connection between each of the straps and the frame a winder motor, the displacement of frame 11 around an initially selected area and its pressure on the body can be remotely controlled. A releasable means will preferably be provided to enable manually positioning frame 11 in an initial position.

Figure 3:
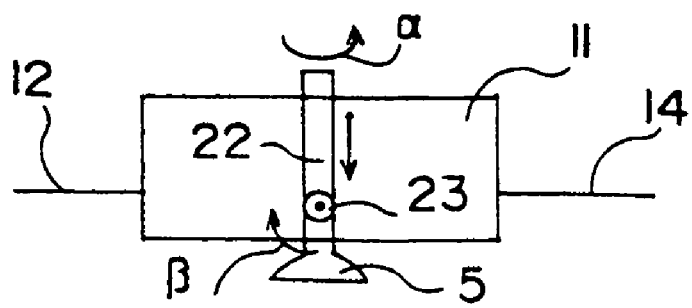
FIG. 3 is a partial view of an example of a supporting frame of an echographic probe usable according to the present invention.

As shown in FIG. 3, frame 11 may be a package in which echographic probe 21 is mobile in a remotely controllable way. For example, the probe is bound to an arm 22 mobile in the package perpendicularly thereto, to apply a higher or lower pressure between the probe and the patient. Arm 22 will for example be mobile in rotation around its axis (direction $\alpha$) and with respect to this axis around a joint 23 (direction $\beta$). Conventionally, more or fewer degrees or freedom may be provided.

Figure 4:
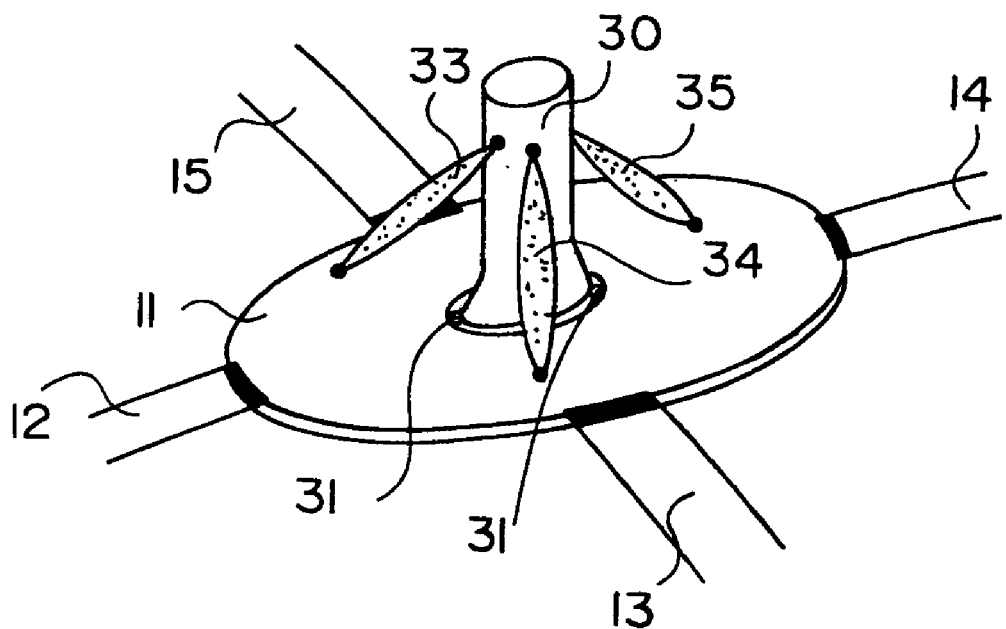
FIG. 4 is a partial view of another example of an echographic probe-supporting frame usable according to the present invention.

In the embodiment of FIG. 4, frame 11 is a simple plate on which is assembled, for example by a ball joint system 31, an echographic probe 30. The probe body may be displaced and oriented with respect to the plate by means of an assembly of automatic actuators 33, 34, 35. The pneumatic actuators are for example inflatable tubes currently called "artificial muscles", the length of which decreases when they receive a gas under pressure.

Although this is not described in detail herein, means for controlling the various motors and other previously-described remotely controllable means with the displacements of a master unit handled by a remote operator communicating with the drive system just described by any means such as a radio link, an optical cable link, or other, are known in the art.

Various modes of action on the controlled device may be provided.

The device displacement may be completely automated and correspond to a predetermined strategy. This strategy for example aims at fulfilling a criterion of complete scanning by the echographic probe of a selected anatomic volume.

The displacement of the device may involve an expert who uses the images generated by the device or physical information characterizing the device behavior to adapt his medical strategy. The physical information may especially be:

position information, provided by video cameras, a three-dimensional locator, or length encoders of the flexible binding means, physiological signals generated by the device or by sensors coupled to the device, or measurements of the pressure or of the mechanical stress exerted by the environment on the system.

To ensure the patient's security, and avoid for excessive pressures to be applied to him by the probe or its frame, it may be provided for straps 12–15 to have a certain resilience, or to be bound by rupture systems. Any other passive security system may be provided to avoid for the slave to exert on the patient any force or pressure beyond predetermined limits. Similarly, the elements of displacement between the probe and the frame may be flexible, and possibly resilient.

The system of FIG. 2 is an example only of implementation of the present invention. The basic aspect of the present invention is that it provides a system enabling remote control of the sliding and orientation of a therapeutic or diagnosis device on the human body. Many alternative embodiments may be provided to ensure this function. For example, the straps may be replaced by any other "thread" system possibly driven by "artificial muscles" (inflatable tubes tightened in braids exerting variable tractions under the effect of pressure variations generated by valves likely to be controlled by computer means), or by rigid cradle and spring systems. Of course, it will further have to be provided for the various system components in contact with the skin to slide thereon. The straps may for example, in the case of the specific described embodiment, be soaked with an echographic gel.

It is particularly simple, for a local operator or for the patient himself, to rapidly release the system by means of an easily accessible control to interrupt the remotely controlled displacement if the system should become painful, or to displace the frame as selected and required by the distant expert to whom the patient is linked by an audio and preferably video link.

An application to an endoscopic system will be implemented in an analogous manner, the information feedback between the endoscope and the remote expert corresponding to the very image provided by the endoscopic camera.

In the context of an application such as the placing of a puncture needle, the image feedback to the distant expert may come from one or several video cameras observing the general scene, from a tri-dimensional locator able to follow the position or the orientation of the needle, or from a specific imaging system (X-rays, scanner, MRI . . . ).

What is claimed is:

1. A remotely controllable system for positioning on a patient an observation and/or intervention device including:
   a patient's support on which the patient resides during a diagnosis;
   a frame to which the device is bound with a number of degrees of freedom;
   a plurality of flexible connection means, each of which is arranged for flexibly connecting the frame and a point adapted to be attached to the patient's support or to the patient himself;
   connecting the frame to different connection points on the patient's support remotely controlled means for modifying the length/tension of the connection means; and
   means for remotely observing the device behavior, capable of controlling said remotely controlled means.

2. The system of claim 1, wherein each of the flexible connection means is one of a cable, a thread or a strap.

3. The system of claim 2, wherein each of the flexible connection means is resilient.

4. The system of claim 2, wherein the remotely controlled means include winder motors.

5. The system of claim 1, wherein the remotely controlled means include artificial muscles.

6. The system of claim 1, wherein the connection between the frame and the device is ensured by remotely controlled flexible connection means.

7. The system of claim 1, wherein the device is an echographic probe, and said remote observation means further enable observation of the echographic image.

8. The system of claim 1, wherein the device is an endoscope, and the remote observation means further enable observation of the endoscopic image.

9. The system of claim 1, wherein the device is a needle holder, and the remote observation means enable observation of an image from X-rays, scanners, or MRIs.

10. The system of claim 1, wherein the remotely controlled means for modifying the length/tension of the connection means is controlled by the patient by an audio link.

11. A system for remotely controlling position of a diagnostic device on a patient, the system comprising:
    a patient's support on which the patient resides during a diagnosis;
    a frame on which the diagnostic device is attached;
    a plurality of flexible connection means, each of the flexible connection means connecting the frame to different connection points on the patient's support;
    remotely controlled means for adjusting the length and tension of each of the flexible connection means, wherein changing the length and tension of each of the flexible connection means changes the position of the diagnostic device on a patient.

12. The system of claim 11, wherein adjusting the length and tension of the plurality of flexible connection means define direction of the diagnostic device as it moves from one position to another position on the patient.

13. The system of claim 11, wherein each of the flexible connection means is one of a cable, a thread or a strap.

14. The system of claim 11, wherein the plurality of flexible connection means consists of four flexible connections.

* * * * *